US008241264B2

(12) United States Patent
Sjogren et al.

(10) Patent No.: US 8,241,264 B2
(45) Date of Patent: Aug. 14, 2012

(54) METHOD AND APPARATUS FOR AUTOTRANSFUSION

(75) Inventors: Johan Sjogren, Billdal (SE); Erik Andreen, Torslanda (SE); Sanna Grange-Jansson, Askim (SE); Martin Nilsson, Hovas (SE)

(73) Assignee: Astra Tech AB, Molndal (SE)

( * ) Notice: Subject to any disclaimer, the term of this patent is extended or adjusted under 35 U.S.C. 154(b) by 360 days.

(21) Appl. No.: 11/663,749

(22) PCT Filed: Oct. 14, 2005

(86) PCT No.: PCT/SE2005/001541
§ 371 (c)(1),
(2), (4) Date: May 7, 2007

(87) PCT Pub. No.: WO2006/041406
PCT Pub. Date: Apr. 20, 2006

(65) Prior Publication Data
US 2008/0015485 A1      Jan. 17, 2008

(30) Foreign Application Priority Data

Oct. 14, 2004  (SE) ...................................... 0402500

(51) Int. Cl.
*A61B 19/00*   (2006.01)
(52) U.S. Cl. ...................................... 604/403; 604/4.01
(58) Field of Classification Search ........ 604/4.01–6.01, 604/6.15, 391, 403, 317, 319–321, 323, 350, 604/405; 251/4, 9
See application file for complete search history.

(56) References Cited

U.S. PATENT DOCUMENTS

| | | | |
|---|---|---|---|
| 3,896,733 A | | 7/1975 | Rosenberg |
| 3,993,067 A | | 11/1976 | Schachet et al. |
| 4,006,745 A | | 2/1977 | Sorenson et al. |
| 4,033,345 A | * | 7/1977 | Sorenson et al. ............ 604/6.09 |
| 4,599,093 A | * | 7/1986 | Steg, Jr. ............................ 95/46 |
| 4,898,572 A | | 2/1990 | Surugue nee Lasnier et al. |
| 4,909,780 A | * | 3/1990 | Ouriel et al. .................. 604/6.15 |
| 4,932,629 A | * | 6/1990 | Rodomista et al. ................ 251/4 |
| 5,024,613 A | * | 6/1991 | Vasconcellos et al. ....... 604/6.15 |
| 5,100,376 A | * | 3/1992 | Blake, III ....................... 604/6.1 |

(Continued)

FOREIGN PATENT DOCUMENTS
EP        0351980 A2      1/1990
(Continued)

*Primary Examiner* — Tatyana Zalukaeva
*Assistant Examiner* — Benedict L Hanrahan
(74) *Attorney, Agent, or Firm* — Birch, Stewart, Kolasch & Birch, LLP

(57) ABSTRACT

An apparatus for collecting and salvaging blood includes: a first chamber with a below atmosphere internal pressure for continuous collection of blood through an inlet port; a second chamber for receiving blood from the first chamber through a connection channel; a channel valve manually controllable to close the connection channel; and a control for simultaneously controlling the channel valve and the internal pressure of the second chamber between an internal pressure corresponding to the internal pressure of the first chamber and ambient air pressure, wherein the control is arranged to provide an internal pressure corresponding to the internal pressure of the first chamber to the second chamber through a passageway separated from the connection channel for providing blood from the first chamber to the second chamber.

31 Claims, 9 Drawing Sheets

U.S. PATENT DOCUMENTS

| | | | |
|---|---|---|---|
| 5,634,893 A * | 6/1997 | Rishton | 604/6.1 |
| 5,853,398 A * | 12/1998 | Lal et al. | 604/250 |
| 5,885,261 A * | 3/1999 | Longo et al. | 604/319 |
| 6,250,331 B1 * | 6/2001 | Nardi | 137/517 |
| 6,475,176 B2 * | 11/2002 | Fini | 604/6.15 |
| 6,840,492 B1 * | 1/2005 | Boyne-Aitken | 251/7 |

FOREIGN PATENT DOCUMENTS

| | | |
|---|---|---|
| EP | 0743071 A2 | 11/1996 |
| EP | 1 031 357 A2 | 8/2000 |
| JP | 2-65868 A | 3/1990 |
| JP | 9-10299 A | 1/1997 |
| JP | 9-66107 A | 3/1997 |

* cited by examiner

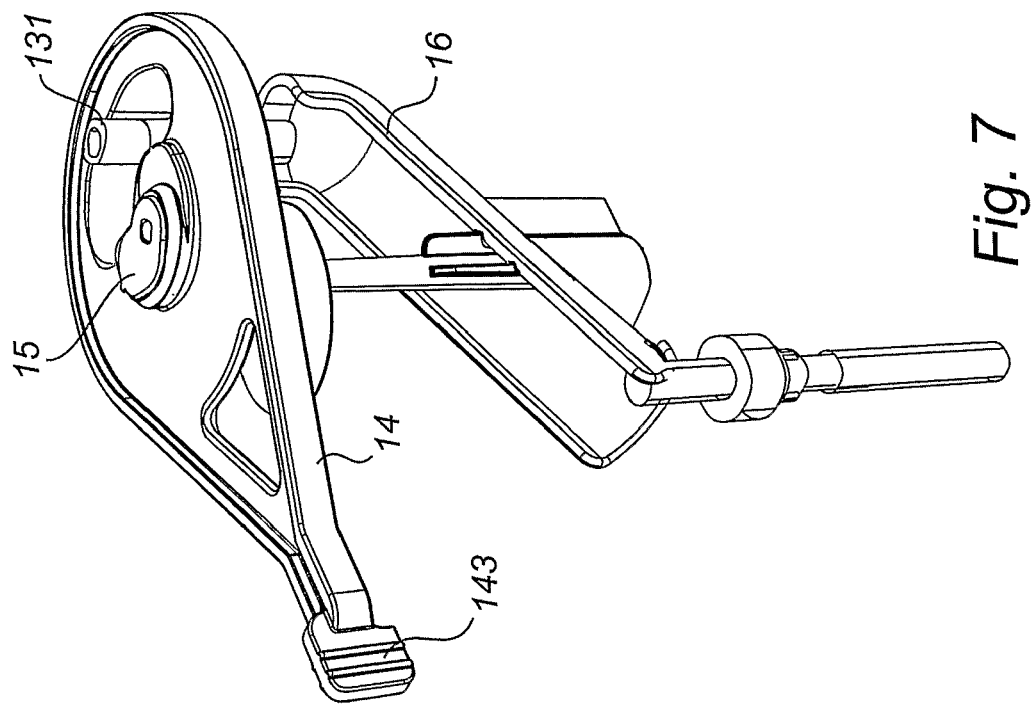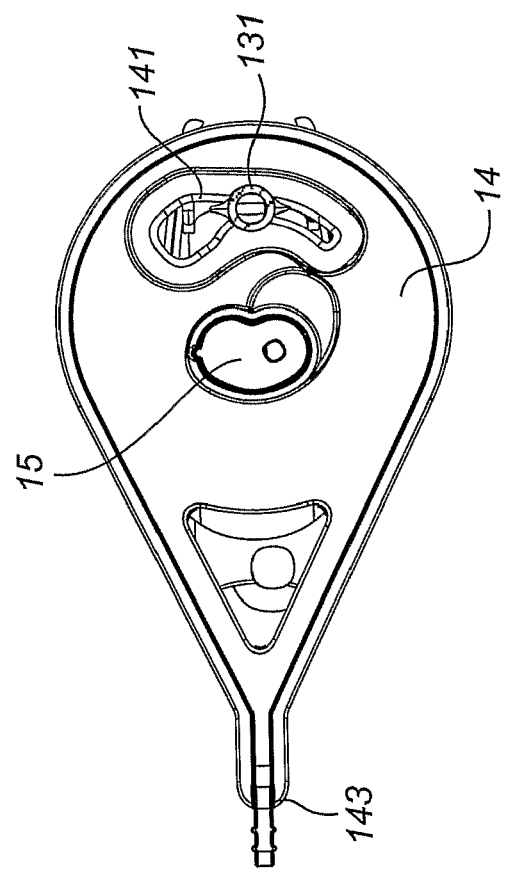

METHOD AND APPARATUS FOR AUTOTRANSFUSION

FIELD OF THE INVENTION

The present invention relates to a medical equipment, and in particular to an autotransfusion apparatus for collecting blood in a way enabling reintroduction of the blood into the patient. Further, the invention relates to a corresponding method.

BACKGROUND OF THE INVENTION

When a patient loses a significant amount of blood from a wound or operation site, that blood must be replaced. Due to the risk of blood-transmitted diseases, however, it is desirable to limit the amount of donated blood that is infused. The supply of replacement blood could also be limited. It is therefore advantageous to collect the blood lost by the patient, processing the blood with a recovery system to remove any bone chips, blood clots or lipids within the collected blood, and then reinfusing it back into the patient. Salvaging a patient's own blood limits the amount of donated blood the patient must receive, thereby reducing the risk of exposure to disease, and reduces the need for replacement blood.

Blood-recovery systems typically suction blood from the wound or operation site through a suction hose leading to a collection reservoir, which is also connected to a vacuum source. The vacuum draws blood into the reservoir via the suction hose. Ordinarily, the path from the hose to the reservoir passes through one or more blood filters. Once the collection reservoir is full, the blood is drained into a collection bag for reinfusion or later use. Generally, in order to drain the blood from the reservoir, it is necessary to break the vacuum within the reservoir by, for example, venting the reservoir to the atmosphere. In many blood-recovery systems, this operation necessarily interrupts the flow of blood since a vacuum is necessary to draw blood into the reservoir.

Various attempts have been made to provide apparatus capable of collecting blood from a patient continuously. For example, U.S. Pat. No. 5,634,893 and U.S. Pat. No. 4,033,345 discloses apparatuses for continuously collecting blood from a patient while simultaneously draining the processed blood from the reservoir. The apparatus is U.S. Pat. No. 5,634,893 includes a first chamber for collecting blood and a lipid separator, which separates undesirable lipids or other buoyant substances from the collected blood, arranged in said first chamber. A vacuum port on the first chamber couples the chamber to a vacuum source. The first chamber is connected to a second chamber into which collected blood drains, located below the first chamber so that blood can drain into the second chamber by gravity through a duckbill drain valve. A selector valve selectably couples the second chamber either to the vacuum source or to a vent. The drain valve closes when the second chamber is vented while the first chamber is coupled to the vacuum source, thereby isolating the chambers from one another and permitting the first chamber to remain under vacuum even as the vented second chamber drains into a blood bag.

However, the known apparatuses capable of collecting blood continuously while allowing drainage of the collected blood for reinfusion are subject to several problems. For example, most such known systems are expensive and mostly only capable of use for a limited time, and only on one single occasion. Further, said known systems are often complicated to use, requiring extensive skills from the operator. Specifically, the system disclosed in U.S. Pat. No. 5,634,893 is intended for one time use, and for use during a limited time period. After a certain time of operation the first chamber will become clogged by lipids and other buoyant substances from the collected blood. Further, the one-way valve arranged between the first and second chamber is unreliable, and problems with inadequate closure might be expected.

SUMMARY OF THE INVENTION

It is therefore an object of the present invention to provide an apparatus for collecting and salvaging blood, and a method for operation of the same, which alleviates at least some of the above-discussed problems of the prior art. This object is achieved with an apparatus and a method according to the appended claims.

According to a first aspect of the invention, there is provided an apparatus for collecting and salvaging blood comprising:
a first chamber for collecting blood through an inlet port;
a second chamber for receiving blood from the first chamber through a connection channel;
a channel valve manually controllable to close the connection channel; and
a control means for simultaneously controlling the channel valve and the internal pressure of the second chamber.

This inventive apparatus has proven remarkably easy to operate and effective in use, and still relatively cost-effective to produce. The manually controllable channel valve could be made very reliable and efficient. At the same time the control means for simultaneously controlling the channel valve and the internal pressure of the second chamber provides means for very efficient operation of the apparatus. With one single operation, and by use of only one hand, the operator could switch between two operation modes: a first operation mode in which the channel valve is open and the second chamber is subjected to low pressure, preferably vacuum, whereby blood is conveyed from the first chamber to the second chamber through the channel valve; and a second operation mode in which the channel valve is closed and the second chamber is subjected to ambient air pressure, whereby blood is drained from the second chamber while continuing to collect blood in the first chamber.

Further, the relatively simple construction of the new apparatus, e.g. comprising only two chambers, makes the product small and convenient to use, and also relatively cost-effective to produce.

Preferably, a channel connecting the second chamber with ambient air pressure is provided, wherein the control means for simultaneously controlling the channel valve and the internal pressure of the second chamber is arranged to control the passage provided by said channel between an opened and a closed disposition. Further, it is preferred that a channel connecting the second chamber directly to a vacuum source is provided, wherein the control means for simultaneously controlling the channel valve and the internal pressure of the second chamber is arranged to control the passage provided by said channel between an opened and a closed disposition. In that case, the same vacuum source may be used to provide vacuum to the first and second chamber, wherein the channel connecting the second chamber directly to the vacuum source is arranged to by-pass the first chamber.

Hereby, the control means for simultaneously controlling the channel valve and the internal pressure of the second chamber may be arranged to control the internal pressure of the second chamber through a passageway separated from the connection channel for providing blood from the first chamber to the second chamber, which is advantageous since it provides a very fast, reliable and efficient pressure control of the second chamber. At the same time, the separation of the internal pressure control from the connection channel for providing blood from the first chamber to the second chamber protects the blood from being damaged, and in particular it prevents hemolysis. It also prevents blood stopping and flow stagnation, which otherwise may occur when the first chamber is filled too rapidly or when the blood level in the first chamber is too high.

In a preferred embodiment, the apparatus further comprises a lipid separator arranged in the second chamber for separating the blood from lipids before the release through the release port.

By the arrangement of the lipid separator in the second chamber, it is possible to provide a very efficient separation and cleaning of the blood, and to allow release of the separated lipids and other buoyant substances from the chamber when the concentration is too high. Consequently, the apparatus could be used during an extended period of time, and could also be used for repeated re-use.

According to another aspect of the invention, there is provided an apparatus for collecting and salvaging blood comprising:

a first chamber for collecting blood through an inlet port;

a second chamber for receiving blood from the first chamber through a connection channel;

a channel valve manually controllable to close the connection channel;

an outlet port to release blood from the second chamber; and a lipid separator arranged in the second chamber for separating the blood from lipids before the release through the release port.

This inventive apparatus has also proven remarkably easy to operate and effective in use, and still relatively cost-effective to produce. By the arrangement of the lipid separator in the second chamber, it is possible to provide a very efficient separation and cleaning of the blood, and to allow release of the separated lipids and other buoyant substances from the chamber when the concentration is too high. Consequently, the apparatus could be used during an extended period of time, and could also be used for repeated re-use.

As discussed previously, the apparatus preferably comprises a control means for simultaneously controlling the channel valve and the internal pressure of the second chamber.

Further, the connection channel preferably comprises a tube with flexible walls and the channel valve comprises means for compressing said tube, thereby closing the channel. Hereby, a very effective and reliable closure could be provided by relatively simple means. Further, the channel valve could comprise a narrowing slit opening, said slit opening being displaceable in a direction being parallel to direction of the opening and perpendicular to the length direction of the tube. In an advantageous embodiment the slit opening could be arranged in a rotatable plate-like member being arranged between the first and the second chamber.

The internal pressure of the second chamber is preferably controllable by means of a selector valve selectively connecting the second chamber to vacuum or ambient air pressure. Hereby, the internal pressure of the second chamber could be controlled adequately between at least two different states: a vacuum state in which blood could be transferred from the first chamber to the second chamber, and a atmosphere pressure state, in which blood could be released from the second chamber. The selector valve preferably comprises a displaceable packing arranged on a input port to the second chamber, the packing in a first disposition allowing vacuum from a vacuum source to reach the input port and in a second disposition ambient air pressure from an ambient air provision to reach the input port. Said selector valve could easily be integrated with the rotatable plate-like member discussed above for controlling the channel valve between the first and second chamber.

The lipid separator could comprise an internal chamber within the second chamber, said chamber comprising a input opening debouching into the second chamber and the release port opening for draining blood, said release port opening being arranged higher than the input opening. This mechanical separation has proven surprisingly effective. Preferably, the internal chamber further comprises a vent fluidly connecting the upper part of the internal chamber with the upper region of the second chamber. Hereby, the pressure in the internal chamber is automatically the same as the overall internal pressure of the second chamber, whereby siphon effects and the like are avoided.

The first chamber could further comprise a vacuum port for connecting the first chamber to a vacuum source. Further, the first chamber could comprise a low pressure safety valve, said safety valve being arranged to automatically increase the pressure in the first chamber in case the internal pressure of the first chamber is below a certain low pressure threshold value. Preferably, the low pressure safety valve is arranged to produce an alarm when activated. By means of this arrangement, the low pressure could be automatically controlled not to be lower than a predetermined level which could jeopardize the operation or the equipment. The safety valve could e.g. comprise a membrane that breaks at a certain pressure difference, a so-caller crack resistance valve. Further, the alarm could be used to get the operators attention that the automatic safety valve is used, whereby appropriate actions could be taken.

Further, the first chamber preferably comprises at least one filter for filtering the input blood before it reaches the connection channel leading to the second chamber. Hereby, the input blood could be cleansed by removal of bone chips, blood clots and the like.

The second chamber could further comprise a second release opening for release of blood which has not passed the lipid separator. Hereby, the ordinary, first release port could be used only for blood to be reintroduced to the patient, whereas lipids and the like could, when necessary, be released through the second release opening. The ordinary, first release port could preferably be connected to a transfusion bag in fluid communication with the outlet port of the second chamber, to receive released blood therefrom.

According to still another aspect of the invention, there is provided a method for collecting and salvaging blood, the method comprising the steps of:

providing a blood-collection apparatus comprising first and second chambers connected by connection channel, said channel being manually closeable by a channel valve;

continuously collecting blood in the first chamber while subjecting the first chamber to a vacuum;

controlling the internal pressure of the second chamber between vacuum and ambient air pressure;

providing control means for simultaneously controlling the internal pressure of the second chamber and the channel valve in the connection channel;

operating the blood-collecting apparatus in two operation modes, said modes being selectable with said control means, wherein in a first operation mode the channel valve is open and the second chamber is subjected to vacuum, whereby blood is conveyed from the first chamber to the second chamber through the channel valve; and wherein in a second operation mode the channel valve is closed and the second chamber is subjected to ambient air pressure, whereby blood is drained from the second chamber while continuing to collect blood in the first chamber.

With this aspect of the invention, similar and corresponding advantages as discussed above with reference to the other aspects of the invention are obtained.

The present invention provides a simple and compact apparatus for collecting and processing salvaged blood, and which facilitates simultaneous collection and drainage of blood without interrupting the incoming flow. The above-discussed and other aspects of the invention will be apparent from and elucidated with reference to the embodiments described hereinafter.

BRIEF DESCRIPTION OF THE DRAWINGS

For exemplifying purposes, the invention will be described in closer detail in the following with reference to embodiments thereof illustrated in the attached drawings, wherein:

FIG. 6 is a top view of the rotatable control member of the apparatus in FIG. 1;

FIG. 7 is a side view of the rotatable control member and the lipid separator of the apparatus in FIG. 1;

DESCRIPTION OF PREFERRED EMBODIMENTS

Figure 1:
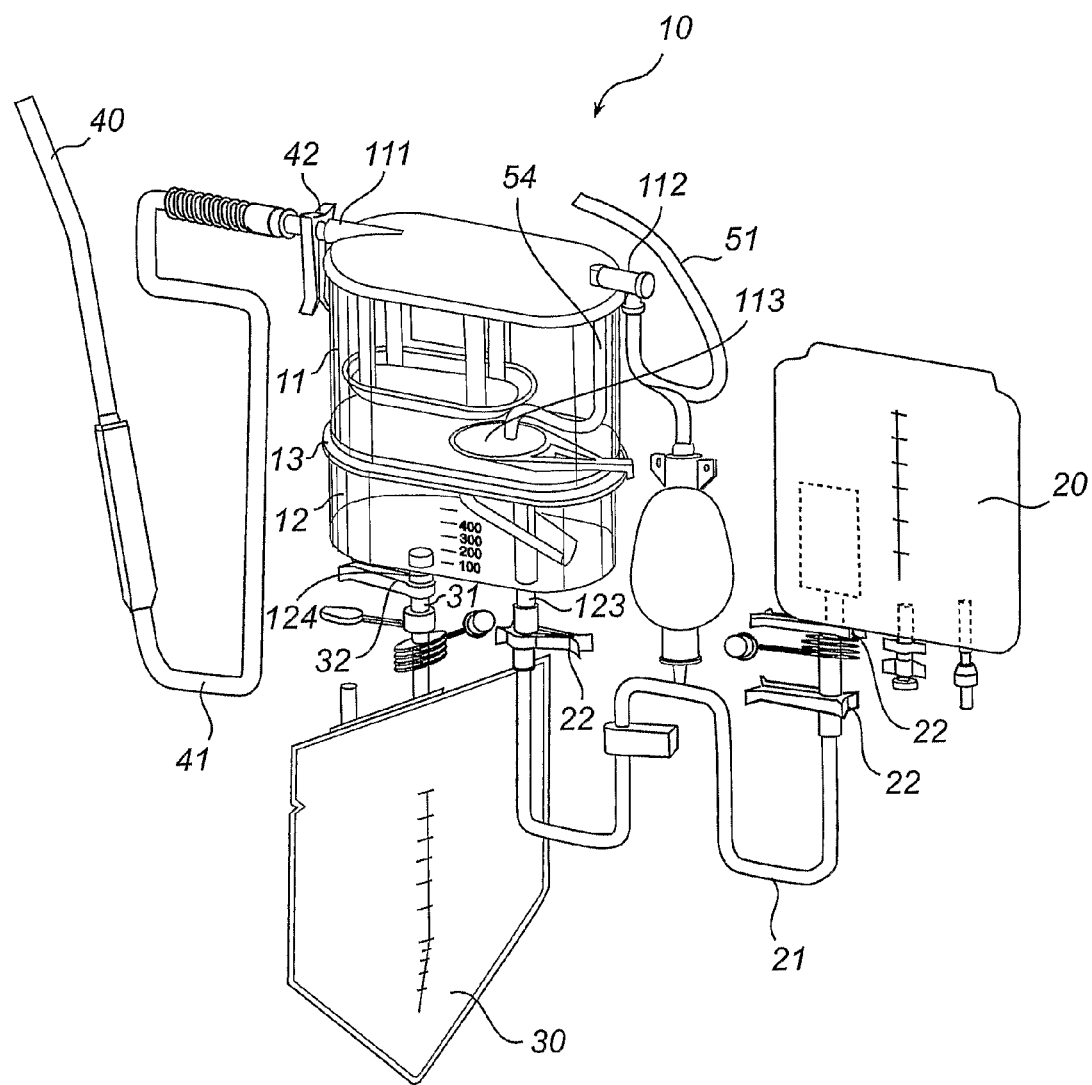
FIG. 1 is a schematic illustration of an apparatus according to an embodiment of the invention.
Figure 2:
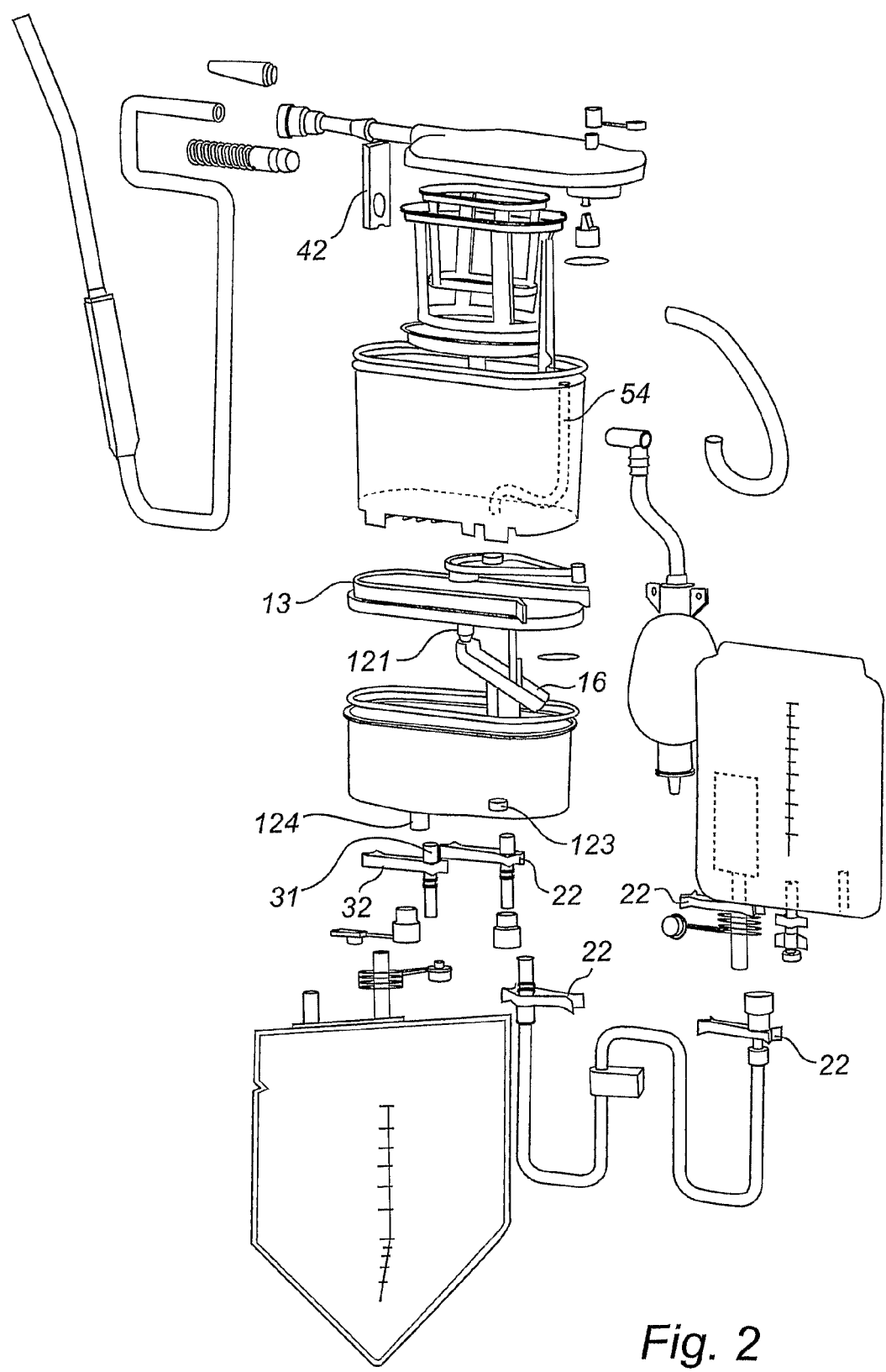
FIG. 2 is an exploded view of the apparatus in FIG. 1.

With reference to FIGS. 1 and 2, the invention generally relates to an autotransfusion apparatus 10 in accordance with the present invention for collecting and processing blood from a wound or operation site. The apparatus includes a reservoir 10, including a first, upper chamber 11 and a second, lower chamber 12. Between the upper and lower chamber an intermediate member 13 is arranged, which is discussed in more detail in the following. The first, upper chamber 11 comprises a blood input port 111 and a vacuum port 112 arranged on the upper region of the chamber, and a blood output port 113 arranged at the bottom end of the chamber. The second, lower chamber 12 comprises a blood input port 121 and a vacuum port 122 arranged on the upper region of the chamber. The blood input port 121 is connected to the outlet port 113 or the first chamber. Further, the second chamber comprises first and second blood output ports 123, 124 arranged at the bottom end.

A transfusion blood bag 20 for collecting the processed blood is coupled to the first blood output port 123 of the lower chamber 12, e.g. by a section of blood-compatible tubing 21.

One or several valves, such as clamps 22 could be arranged on the tubing to enable opening and closing of the fluid channel.

A waste blood bag 30 for collecting separated waste blood products could be coupled to the second blood output port 124 of the lower chamber 12, e.g. by a section of blood-compatible tubing 31. One or several valves, such as clamps 32 could be arranged on the tubing to enable opening and closing of the fluid channel.

Suction means for suctioning blood from a wound or operation site, such as a a suction mouthpiece 40 and a flexible blood-compatible suction tube 41, is coupled to the blood input port 111 of the upper chamber 11. A valve 42, such as a check valve or a clamp, could be arranged on the suction tube to provide means for opening and closing the input port 111.

The vacuum port 112 of the first chamber is connected to a vacuum source. To this end, an external vacuum source could be used, such as a general hospital vacuum system, and connected to the vacuum port through a tubing 51. Alternatively or additionally, a local vacuum source, such as a compressible flexible bladder or bellow 52 could be used, connected to the vacuum port through a tubing 53.

The vacuum port 122 of the second chamber is also connected to a vacuum source. Preferably, the same vacuum source is used for both the upper and lower chamber. In such an embodiment, a vacuum transfer tubing 54 could be arranged to connect the vacuum port 112 of the first chamber to the vacuum port 122 of the second chamber. Said tubing 54 is preferably arranged entirely inside the first chamber.

Figure 3:
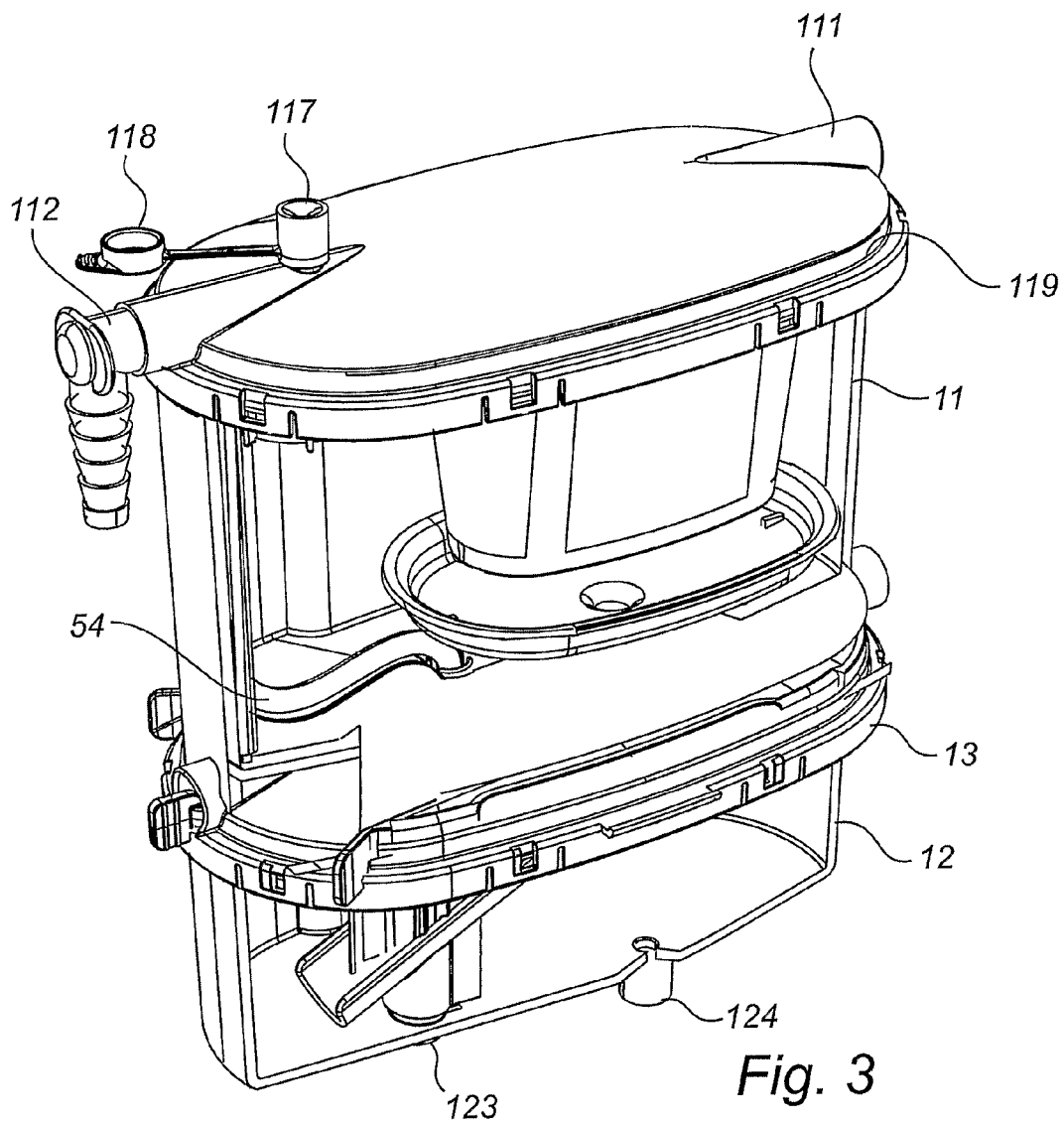
FIG. 3 is a partly broken side view seen of the collection chambers of the apparatus of FIG. 1.
Figure 4:
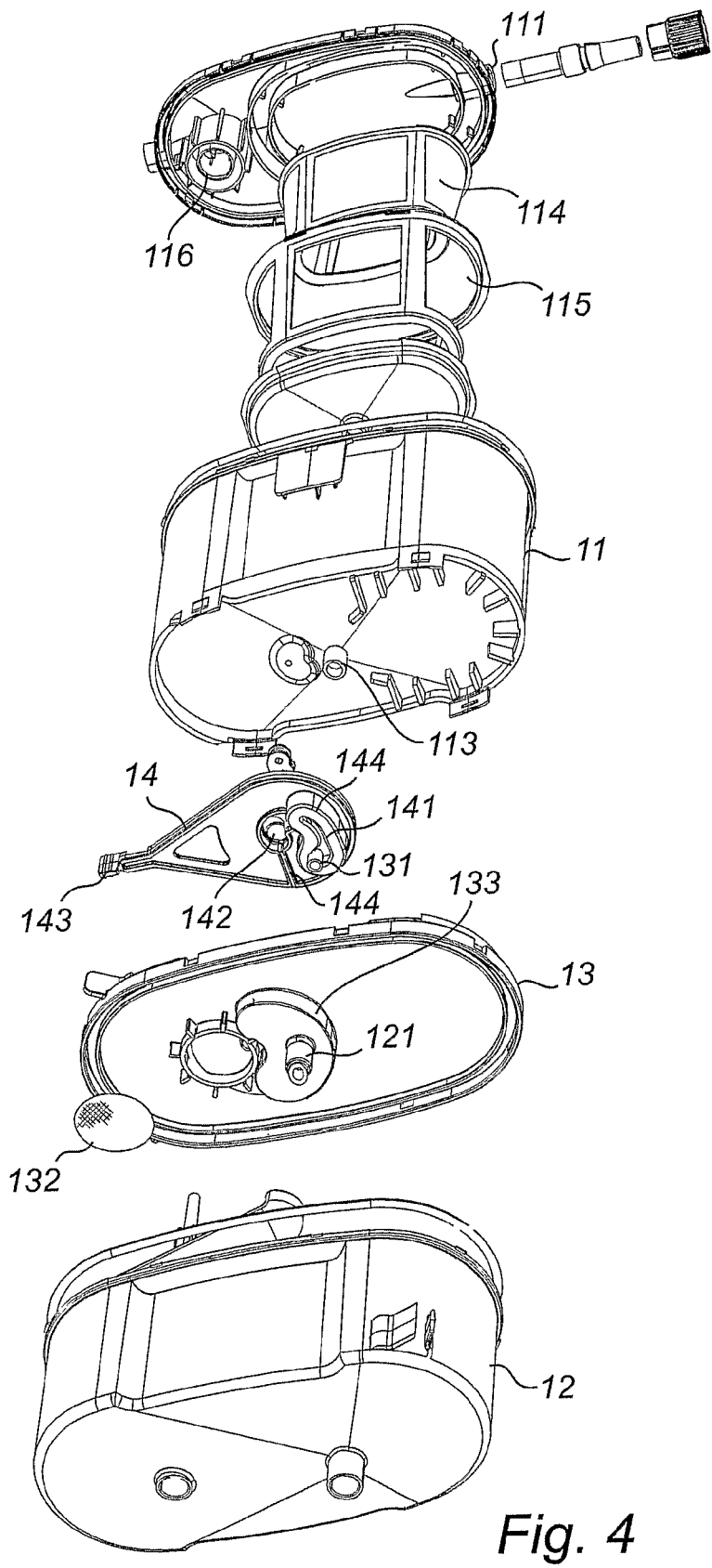
FIG. 4 is an exploded side view seen from below of the collection chambers of FIG. 3.
Figure 5:
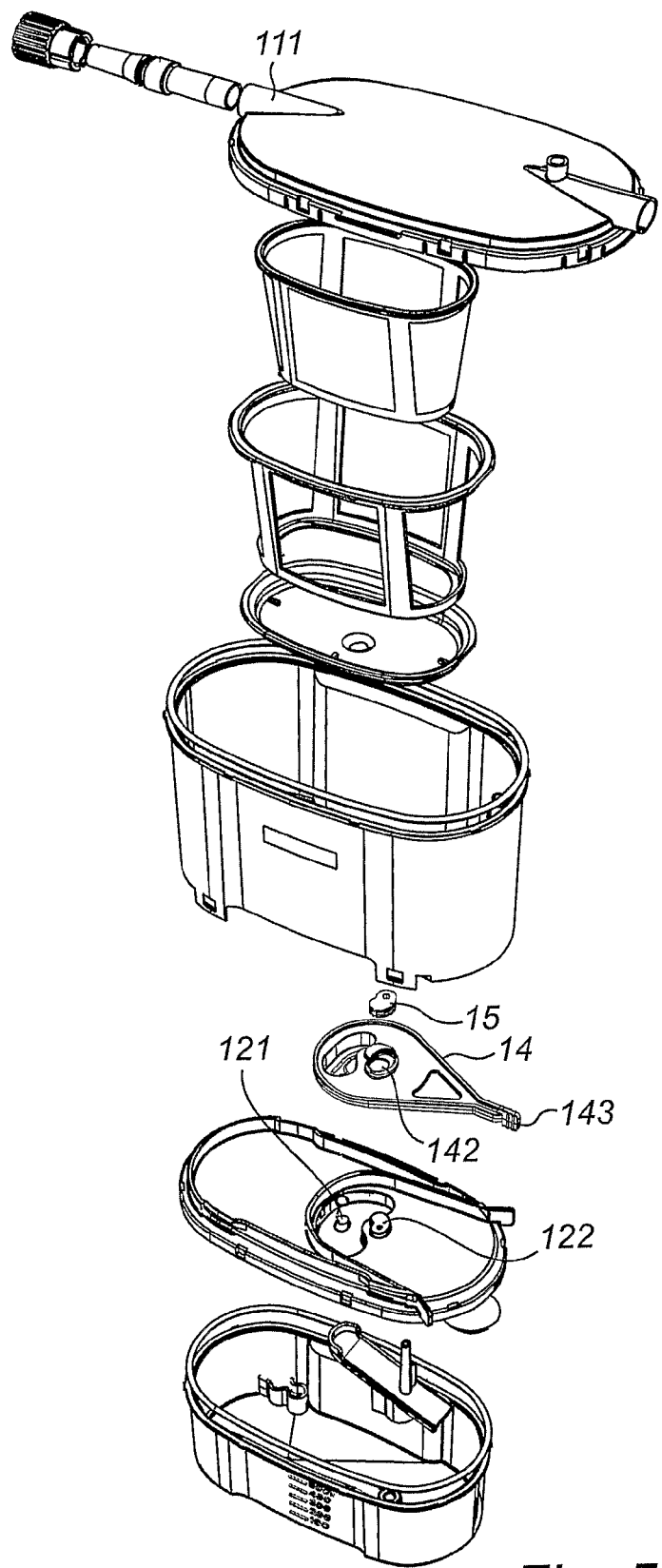
FIG. 5 is an exploded side view seen from above of the collection chambers of FIG. 3.

The construction and functionality of the reservoir 10 will now be discussed in greater detail with reference to FIGS. 3-5.

The blood received from the patient is received to the first chamber 11 through the input port 111. The received blood is first filtered in a particle filter device for removing bone chips, blood clots etc within the collected blood. The filter device preferably comprises two filters, a first coarser filter 114, and a second finer filter 115. The first filter could have a pore size of about 1500 µm, whereas the second filter could have a pore size of about 200 µm. However, alternative filter devices are feasible as well, comprising e.g. only one filter.

The first chamber is during operation constantly maintained in a low pressure state (vacuum), provided through the vacuum port 112. A filter 116 is preferably provided to ensure that no contamination to the received blood is introduced. The filter could e.g. be a hydrophobic filter, as is per se known in the art. Further, a safety valve 117 could be provided, ensuring that the internal pressure of the first chamber is not below a certain threshold value. The safety valve could e.g. comprise a membrane that breaks at a certain pressure difference between the internal pressure of the first chamber and the atmospheric pressure outside the chamber, a so-caller crack resistance valve. The safety valve is further advantageously provided with an alarm functionality, in order to alert the operator that the safety valve is activated. The alarm functionality could preferably be an mechanical alarm means, such as a whistle arranged in the safety means producing an alarm signal when air is passed through the valve. However, other alarm means are feasible as well, such as electronic alarms and the like. Further, the safety valve is preferably deactivatable, whereby the operator is able to deactivate the safety valve when operation with extremely low pressure is required. The means for deactivating the safety valve could e.g. be a cap 118 that could be arranged on the safety valve in order to close the valve channel.

The first chamber is preferably arranged as a trough, having a bottom and a circumferential sidewall made in one piece, and an attachable lid 119. The lid is preferably attachable to the sidewall rim through a mechanical snap connection. However, other ways of attaching the lid are feasible, such as by means of adhesive, welding and the like. Further, a packing (not shown) is preferably arranged between the lid and the sidewall rim in order to ensure a tight sealing.

The second chamber 12 is preferably also arranged as a trough, having a bottom and a circumferential sidewall made in one piece, and an attachable lid. The lid for the second chamber is the intermediate portion 13, to be discussed more thoroughly in the following. The intermediate portion is preferably attachable to the sidewall rim and to the bottom of the first chamber through a mechanical snap connection. However, other ways of attaching the intermediate portion are feasible, such as by means of adhesive, welding and the like. Further, a packing (not shown) is preferably arranged between the intermediate portion and the sidewall rim of the second chamber in order to ensure a tight sealing.

The intermediate portion comprises a vacuum port 122 for the second chamber, and a blood input port 121. The blood input port 121 is connected to the blood output port 113 of the bottom of the first chamber through a flexible tubing 131. The vacuum port 122 of the second chamber is connected to the vacuum port 112 of the first chamber. The vacuum is transferred to an outlet port at the bottom of the first chamber through a tubing 54 arranged inside the first chamber, and connected to the vacuum port 122 of the second chamber through a packing 15 to be discussed more thoroughly in the following. A filter 132 is preferably arranged in the vacuum inlet in order to avoid contamination of the blood.

Between the intermediate portion 13 and the bottom of the first chamber 11, a rotatable plate-like member 14 is arranged. The rotatable member is illustrated in greater detail in FIGS. 6 and 7. The rotatable member is rotatable essentially in the plane of the intermediate portion, i.e. in a direction being perpendicular to the length direction of the tubing 131. The rotatable member comprises a closed end slit 141 through which the flexible tubing 131 is arranged. The slit is narrowing towards one end, whereby rotating of the rotatable member displaces the slit in relation to the tubing, whereby the tubing walls are compressed when at the narrow end of the slit, thereby closing the channel.

Further, the rotatable member comprises an opening 142 for holding a packing 15.

The rotatable member 14 also comprises a manipulation handle 143, which extends past the walls of the chambers, and which is usable for manually rotating the rotatable member. Still further, the rotatable member comprises a downwardly protruding portion 144, which essentially corresponds to a downwardly protruding portion 133 of the intermediate portion. Said protruding portions are arranged to keep the rotatable member in place and to control the rotation motion of the rotatable member.

Figure 9:
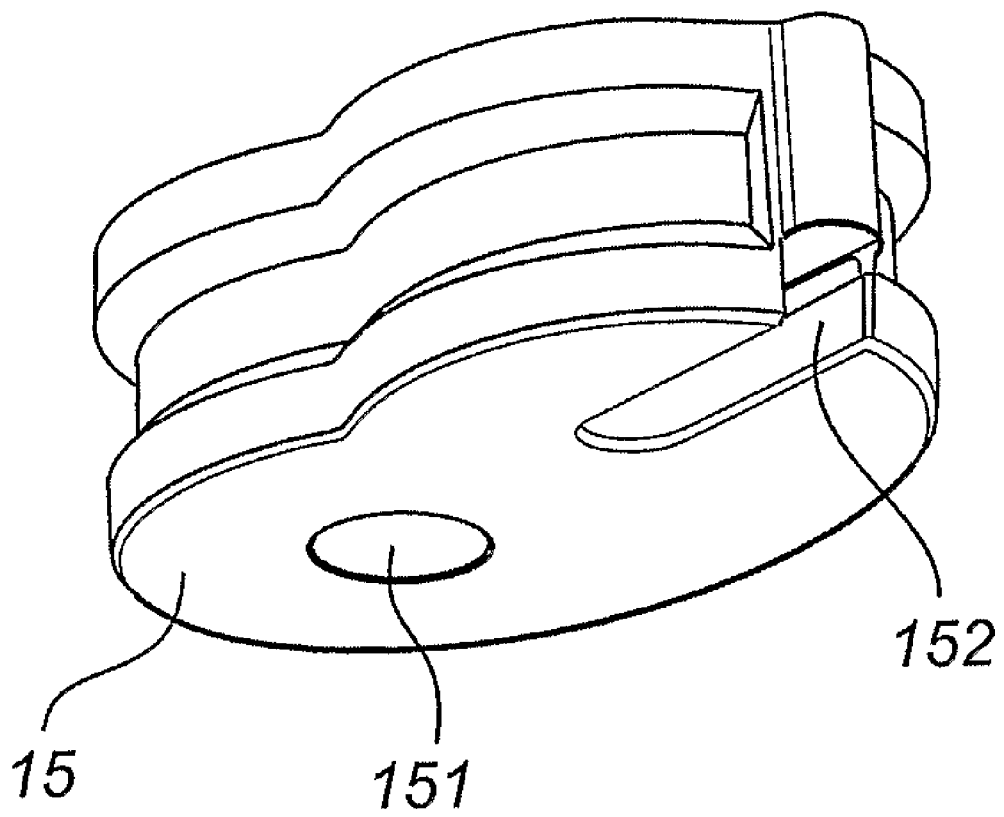
FIG. 9 is a side view from below of the package of the rotatable control member in FIG. 1.

A packing 15 is arranged in the rotatable member for provision of a vacuum valve between the vacuum outlet of the bottom of the first chamber 11 and the vacuum port of the second chamber 12, the latter being arranged in the intermediate portion 13. The packing 15 is illustrated in greater detail in FIG. 9. The packing comprises a through opening 151, providing a channel between the vacuum outlet of the first chamber and the vacuum input of the second chamber. Further, the packing comprises a channel 152 arranged on the side facing the intermediate portion 13. When arranged in the rotatable member, said channel is debouching in a channel 144 provided in the rotatable member. In a first disposition of the rotatable member, the packing is arranged so that the through opening 151 connects the vacuum outlet of the first chamber to the vacuum port of the second chamber. In a second disposition of the rotatable member, the packing is arranged so that it closes the vacuum outlet from the first chamber, and at the same time connects the vacuum port of the second chamber to the ambient atmosphere through the channel 152 and the channel 144. Thus, the internal pressure of the second chamber is controllable by means of the rotatable member to vacuum or ambient air pressure. Hereby, the internal pressure of the second chamber could be controlled adequately between at least two different states: a vacuum state in which blood could be transferred from the first chamber to the second chamber, and a atmosphere pressure state, in which blood could be released from the second chamber.

In the second chamber, a ramp channel 16 is preferably arranged for transferring the blood coming in through the blood input port 121 gently into the second chamber, without damaging the blood.

Figure 8:
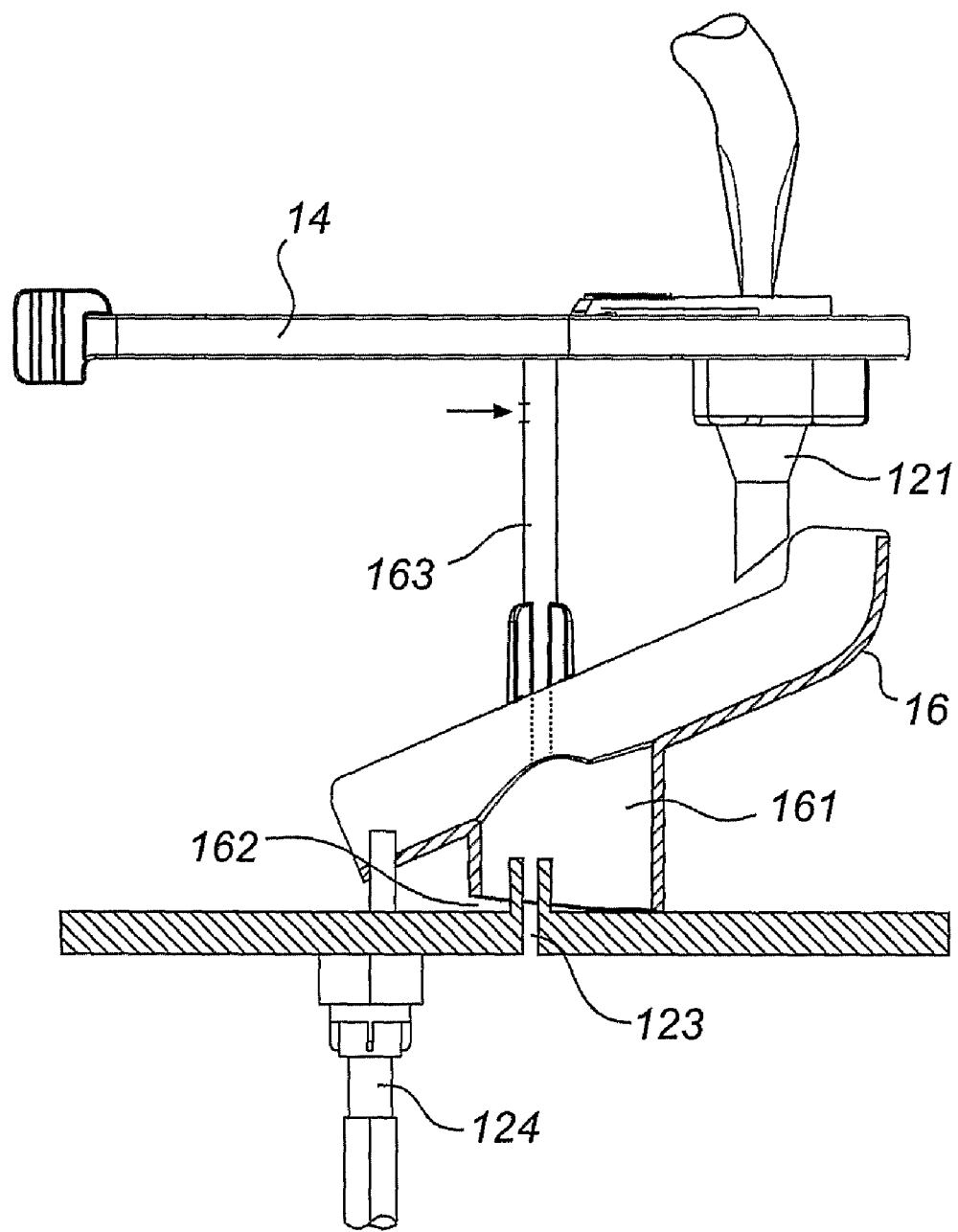
FIG. 8 is a side view of the rotatable control member and the lipid separator of the apparatus in FIG. 1.

Integrated in ramp channel 16 is further a lipid separator. The ramp is illustrated in greater detail in FIG. 8. The lipid separator comprise an internal chamber 161 with an input opening 162 debauching into the second chamber. The internal chamber 161 is arrange above the release port 123 for draining blood from the second chamber, and the release port opening is arranged higher than the input opening. By means of the lipid separator, lipids and other buoyant substances is automatically separated from the collected blood.

Further, a vent 163 is arranged to fluidly connect the upper part of the internal chamber with the upper region of the second chamber. Hereby, the pressure in the internal chamber is automatically the same as the overall internal pressure of the second chamber, whereby siphon effects and the like are avoided.

The reservoir, comprising the chambers 11 and 12 are preferably formed from molded biocompatible plastic. However, other suitable materials, such as stainless steel, can instead be employed. The tubings are preferably fabricated from a flexible and elastomeric material such as silicone or rubber, which allows it to be flexible close upon itself when compressed. The particle filters are preferably a tubular mesh filter element.

In operation, the vacuum source creates a vacuum within upper chamber 11 through the vacuum port 112 and within the lower chamber 12 via the tubing 54, the packing 15 and the vacuum port 122, when the rotatable member 14 is in a first disposition placing the through opening 151 to connect the vacuum outlet of the first chamber in contact with the vacuum port of the second chamber. The vacuum created in upper chamber 11 suctions blood from a patient's wound through suction tube 41 and into upper chamber 11 via blood input port 111 and particle filters 114,115. The filters 114, 115 filters blood clots or particles such as bone chips from the blood entering upper chamber 11.

Blood collecting within upper chamber 11 flows, through the blood output port 113, via the tubing 131 and the blood input port 121 into the lower chamber 12 due to gravity, since the lower and upper chamber are in this operative condition under the same pressure.

When a sufficient amount of blood has been collected in the lower chamber 12, the rotatable member 14 is rotated into the second position such that the tubing 131 is closed and the vacuum port 122 is connected to ambient air pressure. This connects lower chamber 12 to the atmosphere via passage 144, the channel 152 the vacuum port 122 and hydrophobic filter 132, while upper chamber 11 remains connected to vacuum source. Venting lower chamber 12 to the atmosphere increase the pressure in that chamber while upper chamber 11 remains subjected to a vacuum, whereby the apparatus continues to collect blood through suction tube 41.

With the pressure in lower chamber 12 at atmospheric, blood contained in lower chamber 12 could drain freely from lower chamber 12 into blood bag 20 via tubing 21 with clamps 22 open. As the blood flows through opening 162 and into the internal chamber 161, the higher arranged blood release port 123 prevents any lipids floating on top of the blood from passing through the opening.

When lower chamber 12 is sufficiently emptied of the blood, the rotatable member is returned to the first disposition, thereby opening the tubing 131 and reconnecting the second chamber to the vacuum source and subjecting lower chamber 12 to a vacuum.

The blood collected within blood bag 20 can be reinfused back into the patient or stored for later use.

When the concentration of lipids in the second chamber is to high, the second release port 124 could be employed instead of the first release port 123, in order to release the waste into the waste blood bag 30.

Figure 10:
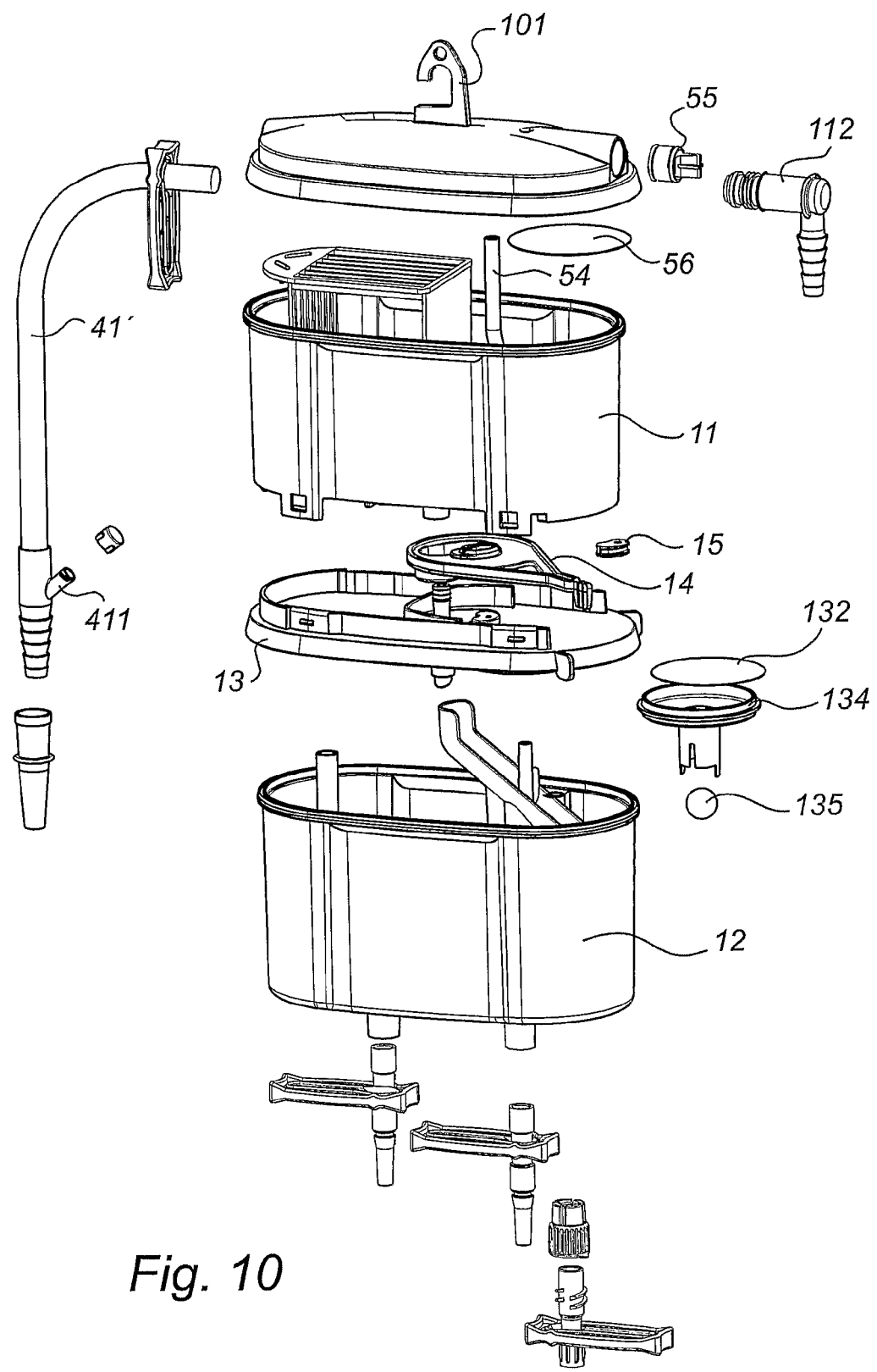
FIG. 10 is an exploded side view seen from above of an alternative embodiment of collection chamber according to the invention.

Another exemplary embodiment is illustrated in FIG. 10. In this embodiment, parts similar or analogue to the ones discussed above in relation to the other embodiments have been denoted with the same reference signs. Further, it is to be understood that parts not specifically discussed in relation to this embodiment may be analogue or similar to corresponding parts of the previously disclosed embodiments, and that corresponding parts are mutually exchangeable between the embodiments.

The suction means for suctioning blood from a wound or operation site comprises a flexible blood-compatible suction tube 41', a an inlet port 411 for supplying citrate to the collected blood. The provision of citrate is preferably controlled in order to obtain desired anti-coagulation properties for the collected blood.

In the first, upper chamber 11, the vacuum port 112 may further be provided with a check-valve 55 and a hydrophobic filter 56, in order to obtain automatic closure of the opening 112 when no vacuum is applied.

In addition a hook 101 or similar mounting means may be arranged for holding the auto transfusion apparatus in an operative position during use.

In the passage connecting the lower chamber 12 with ambient air pressure through the filter 132, a valve 134 may be arranged. This valve is preferably arranged to close automatically when the liquid level in the lower chamber is too high. For example, the valve may comprise a ball 135 which floats in the liquid, and thereby is pushed upwards to block an outlet opening when the liquid level rises. Hereby, leakage of blood from the lower chamber through this channel and/or clotting of the filter is avoided. Similar protection means may also be arranged to protect other filters in the lower or upper chamber. Specific embodiments of the invention have now been described. However, several alternatives are possible, as would be apparent for someone skilled in the art. For example, the vacuum in the first and second chamber may be controllable to be in several different levels. Further, other types of lipid separation means may be employed. Still further, although the present invention has been described in the context of blood recovery and return, the invention can be used to recover or process any biological fluid. In addition, many different types of vacuum sources may be used.

Such and other obvious modifications must be considered to be within the scope of the present invention, as it is defined by the appended claims. It should be noted that the abovementioned embodiments illustrate rather than limit the invention, and that those skilled in the art will be able to design many alternative embodiments without departing from the scope of the appended claims.

The invention claimed is:

1. An apparatus for collecting and salvaging blood comprising:
   a first chamber with a below atmosphere internal pressure for continuous collection of blood through an inlet port;
   a second chamber for receiving blood from the first chamber through a connection channel;
   a channel valve manually controllable to close the connection channel;
   a control means for simultaneously controlling the channel valve and the internal pressure of the second chamber between an internal pressure corresponding to the internal pressure of the first chamber and ambient air pressure, wherein said control means is arranged to provide an internal pressure corresponding to the internal pressure of the first chamber to the second chamber through a passageway separated from the connection channel for providing blood from the first chamber to the second chamber; and
   a rotatable plate member arranged between the first chamber and the second chamber, wherein the rotatable plate member further comprises a manipulation handle, which extends past the walls of the first and second chambers, and which is usable for manually rotating the rotatable plate member.

2. The apparatus of claim 1, further comprising a lipid separator arranged in the second chamber for separating the blood from lipids before the release through the release port.

3. An apparatus for collecting and salvaging blood comprising:
   a first chamber for continuous collection of blood through an inlet port;
   a second chamber for receiving blood from the first chamber through a connection channel;
   a channel valve manually controllable to close the connection channel;
   a passageway to provide an internal pressure corresponding to the internal pressure of the first chamber to the second chamber, wherein said passageway is separated from the connection channel for providing blood from the first chamber to the second chamber;
   an outlet port to release blood from the second chamber;
   a lipid separator arranged in the second chamber for separating the blood from lipids before the release through the release port;
   a control means for simultaneously controlling the channel valve and the internal pressure of the second chamber between an internal pressure corresponding to the internal pressure of the first chamber and ambient air pressure, wherein said control means is arranged to provide an internal pressure corresponding to the internal pressure of the first chamber to the second chamber through a passageway separated from the connection channel for providing blood from the first chamber to the second chamber; and
   a rotatable plate member arranged between the first chamber and the second chamber, wherein the rotatable plate member further comprises a manipulation handle, which extends past the walls of the first and second chambers, and which is usable for manually rotating the rotatable plate member.

4. The apparatus of claim 1, wherein the apparatus is reusable.

5. The apparatus of claim 1, wherein the connection channel comprises a tube with flexible walls and the channel valve comprises means for compressing said tube, thereby closing the channel.

6. The apparatus of claim 5, wherein the channel valve comprises a narrowing slit opening, said slit opening being displaceable in a direction being parallel to direction of the opening and perpendicular to the length direction of the tube.

7. The apparatus of claim 5, wherein a slit opening is arranged in the rotatable plate-like member.

8. The apparatus of claim 1, wherein the internal pressure of the second chamber is controllable by means of a selector valve selectively connecting the second chamber to vacuum or ambient air pressure.

9. The apparatus of claim 8, wherein the selector valve comprises a displaceable packing arranged on a input port to the second chamber, the packing in a first disposition allowing vacuum from a vacuum source to reach the input port and in a second disposition ambient air pressure from an ambient air provision to reach the input port.

10. The apparatus of claim 2, wherein the lipid separator comprises an internal chamber within the second chamber, said chamber comprising a input opening debouching into the second chamber and the release port opening for draining blood, said release port opening being arranged higher than the input opening.

11. The apparatus of claim 10, wherein the internal chamber further comprises a vent fluidly connecting the upper part of the internal chamber with the upper region of the second chamber.

12. The apparatus of claim 1, wherein the first chamber further comprises a vacuum port for connecting the first chamber to a vacuum source.

13. The apparatus of claim 12, wherein the first chamber further comprises a low pressure safety valve, said safety valve being arranged to automatically increase the pressure in the first chamber in case the internal pressure of the first chamber is below a certain low pressure threshold value.

14. The apparatus of claim 13, wherein said low pressure safety valve is arranged to produce an alarm when activated.

15. The apparatus of claim 1, wherein the first chamber further comprises at least one filter for filtering the input blood before it reaches the connection channel leading to the second chamber.

16. The apparatus of claim 2, wherein the second chamber further comprises a second release opening for release of blood which has not passed the lipid separator.

17. The apparatus of claim 1, further comprising a transfusion bag in fluid communication with the outlet port of the second chamber, to receive released blood therefrom.

18. The apparatus of claim 1, further comprising a channel connecting the second chamber with ambient air pressure, wherein the control means for simultaneously controlling the channel valve and the internal pressure of the second chamber is arranged to control a passage provided by said channel between an opened and a closed disposition.

19. The apparatus of claim 1, further comprising a channel connecting the second chamber directly to a vacuum source, wherein the control means for simultaneously controlling the channel valve and the internal pressure of the second chamber is arranged to control a passage provided by said channel between an opened and a closed disposition.

20. The apparatus of claim 19, wherein the same vacuum source is useable to provide vacuum to the first and second chamber, wherein the channel connecting the second chamber directly to the vacuum source is arranged to by-pass the first chamber.

21. A method for collecting and salvaging blood, the method comprising the steps of:
providing the apparatus of claim 1;
continuously collecting blood in the first chamber while subjecting the first chamber to a vacuum;
controlling the internal pressure of the second chamber between vacuum and ambient air pressure;
using the control means to simultaneously controlling the internal pressure of the second chamber and the channel valve in the connection channel;
operating the blood-collecting apparatus in two operation modes, said modes being selectable with said control means,
wherein in a first operation mode the channel valve is open and the second chamber is subjected to vacuum, whereby blood is conveyed from the first chamber to the second chamber through the channel valve; and
wherein in a second operation mode the channel valve is closed and the second chamber is subjected to ambient air pressure, whereby blood is drained from the second chamber while continuing to collect blood in the first chamber.

22. The method of claim 21, further comprising the step of filtering particles from blood entering the first chamber.

23. The method of claim 21, further comprising the step of separating lipids from the blood in the second chamber before drainage of the blood.

24. The method of claim 21, further comprising the step of collecting blood from the second chamber in a transfusion bag.

25. The method of claim 21, wherein the control of the internal pressure of the second chamber comprises controlling of a passage through a channel connecting the second chamber with ambient air pressure.

26. The method of claim 21, wherein the control of the internal pressure of the second chamber comprises controlling of a passage through a channel connecting the second chamber directly to a vacuum source.

27. The method of claim 26, wherein the same vacuum source is useable to provide vacuum to the first and second chamber, wherein the channel connecting the second chamber directly to the vacuum source is arranged to by-pass the first chamber.

28. The method of claim 21, using the apparatus of claim 1 to control the internal pressure of the second chamber through a passageway separated from the connection channel for providing blood from the first chamber to the second chamber.

29. An apparatus for collecting and salvaging blood comprising:
a first chamber with a below atmosphere internal pressure for continuous collection of blood through an inlet port;
a second chamber for receiving blood from the first chamber through a connection channel; and
an intermediate portion arranged between said first and second chambers, said intermediate portion comprising:
a channel valve manually controllable to close the connection channel;
a control means for simultaneously controlling the channel valve and the internal pressure of the second chamber between an internal pressure corresponding to the internal pressure of the first chamber and ambient air pressure, wherein said control means is arranged to provide an internal pressure corresponding to the internal pressure of the first chamber to the second chamber through a passageway separated from the connection channel for providing blood from the first chamber to the second chamber; and a rotatable plate member arranged between the first chamber and the second chamber, wherein the rotatable plate member further comprises a manipulation handle, which extends past the walls of the first and second chambers, and which is usable for manually rotating the rotatable plate member.

30. An apparatus for collecting and salvaging blood comprising:
- a first chamber with a below atmosphere internal pressure for continuous collection of blood through an inlet port;
- a second chamber for receiving blood from the first chamber through a connection channel;
- a channel valve manually controllable to close the connection channel;
- a rotatable plate member arranged between the first chamber and the second chamber, and arranged to simultaneously control the channel valve and the internal pressure of the second chamber between an internal pressure corresponding to the internal pressure of the first chamber and ambient air pressure, wherein said rotatable plate member is arranged to provide an internal pressure corresponding to the internal pressure of the first chamber to the second chamber through a passageway separated from the connection channel for providing blood from the first chamber to the second chamber; and
- wherein the rotatable plate member further comprises a manipulation handle, which extends past the walls of the first and second chambers, and which is usable for manually rotating the rotatable plate member.

31. An apparatus for collecting and salvaging blood comprising:
- a first chamber with a below atmosphere internal pressure for continuous collection of blood through an inlet port;
- a second chamber for receiving blood from the first chamber through a connection channel;
- an intermediate portion arranged between said first and second chambers; and
- a rotatable plate member rotatable in a plane of the intermediate portion, said rotatable plate member comprising:
  - a channel valve manually controllable to close the connection channel;
  - a control means for simultaneously controlling the channel valve and the internal pressure of the second chamber between an internal pressure corresponding to the internal pressure of the first chamber and ambient air pressure, wherein said control means is arranged to provide an internal pressure corresponding to the internal pressure of the first chamber to the second chamber through a passageway separated from the connection channel for providing blood from the first chamber to the second chamber; and
- wherein the rotatable plate member further comprises a manipulation handle, which extends past the walls of the first and second chambers, and which is usable for manually rotating the rotatable plate member.

* * * * *